United States Patent
Bloch et al.

(10) Patent No.: US 7,397,934 B2
(45) Date of Patent: Jul. 8, 2008

(54) REGISTRATION OF THORACIC AND ABDOMINAL IMAGING MODALITIES

(75) Inventors: Isabelle Bloch, Paris (FR); Oscar Camara Rey, Paris (FR); Gaspar Delso, Girona (ES)

(73) Assignee: Segami S.A.R.L., Paris (FR)

( * ) Notice: Subject to any disclaimer, the term of this patent is extended or adjusted under 35 U.S.C. 154(b) by 766 days.

(21) Appl. No.: 10/405,026

(22) Filed: Apr. 1, 2003

(65) Prior Publication Data

US 2003/0216631 A1 Nov. 20, 2003

Related U.S. Application Data

(60) Provisional application No. 60/369,681, filed on Apr. 3, 2002.

(51) Int. Cl.
G06K 9/00 (2006.01)
G06K 9/32 (2006.01)

(52) U.S. Cl. .................................. 382/128; 382/294

(58) Field of Classification Search ......... 382/128–132, 382/294; 600/407, 411, 427, 437; 128/920; 378/4, 8, 15, 901; 250/363.04, 370.08, 370.09
See application file for complete search history.

(56) References Cited

U.S. PATENT DOCUMENTS

| | | | |
|---|---|---|---|
| 5,299,253 A | 3/1994 | Wessels | |
| 5,608,221 A | 3/1997 | Bertelsen et al. | |
| 5,611,000 A * | 3/1997 | Szeliski et al. | 382/294 |
| 5,633,951 A * | 5/1997 | Moshfeghi | 382/154 |
| 5,750,991 A | 5/1998 | Moyers et al. | |
| 5,871,013 A | 2/1999 | Wainer et al. | |
| 5,961,454 A * | 10/1999 | Kooy et al. | 600/407 |
| 5,974,165 A | 10/1999 | Giger et al. | |
| 6,009,212 A | 12/1999 | Miller et al. | |
| 6,040,580 A | 3/2000 | Watson et al. | |
| 6,096,050 A * | 8/2000 | Audette | 606/130 |
| 6,173,201 B1 | 1/2001 | Front | |
| 6,205,347 B1 * | 3/2001 | Morgan et al. | 600/407 |
| 6,405,072 B1 | 6/2002 | Cosman | |
| 6,490,476 B1 * | 12/2002 | Townsend et al. | 600/427 |
| 6,563,941 B1 * | 5/2003 | Aharon et al. | 382/131 |
| 6,807,247 B2 * | 10/2004 | Krishnan et al. | 378/4 |
| 6,950,542 B2 * | 9/2005 | Roesch et al. | 382/128 |
| 7,209,579 B1 * | 4/2007 | Weisenberger et al. | 382/128 |
| 2002/0068864 A1 | 6/2002 | Bishop et al. | |
| 2003/0174872 A1 * | 9/2003 | Chalana et al. | 382/128 |

OTHER PUBLICATIONS

Rueckert et al; "Nonrigid Registration Using Free-Form Deformations: Application to Breast MR Images"; IEEE Transactions on Medical Imaging, vol. 18, No. 8, Aug. 1999.*

(Continued)

*Primary Examiner*—Andrew W. Johns
*Assistant Examiner*—Andrae Allison
(74) *Attorney, Agent, or Firm*—William S. Ramsey

(57) ABSTRACT

This disclosure presents an improved method for registering anatomical medical images and functional medical images. The example deals with the registration of x-ray computer tomography images with positron emission tomography images. The process is characterized by clinically useful registration with minimal computer calculations and minimal delay for computation. A nonrigid B-Spline free form deformation is used in both a preliminary coarse registration and the finished fine registration. Additional steps are used to insure accurate and complete registrations.

10 Claims, 1 Drawing Sheet

OTHER PUBLICATIONS

With et al; "Point-to-Point registration of non-ridig Medical Images using Local Elastic Transformation methods" ; IPA97, 15-1 Jul. 7, 1997, Conference Publication No. 443 0 IEE, 1997.*

Hiller et al "Inter-subject Registration of Functionaland Anatomical Data Using SPM" ; Projet Vista, IRISA/INRIA-CNRS, Rennes, France Functional Imaging Lab,Wellcome Department of Imaging Neuroscience, London, UK.*

Rueckert D et al: "Nonrigid registration using free-form deformations: application to breast MR images" IEEE Transactions on Medical Imaging, Aug. 1999, IEEE, USA, vol. 18, No. 8, pp. 712-721, XP002252407 ISSN: 0278-0062 cited in the application p. 714, right-hand column, paragraph 2-p. 715, left-hand column, paragraph 2.

Baillard C et al: "Cooperation between level set techniques and dense 3D registration for the segmentation of brain structures" Proceedings 15th International Conference on Pattern Recognition. ICPR-2000, Proceedings of 15th International Conference on Pattern Recognition, Barcelona, Spain, Sep. 2000, pp. 991-994 vol. 1, XP010533714 2000, Los Alamitos, CA, USA, IEEE Comput. Soc, USA ISBN: 0-7695-0750-6.

Thevenaz P et al: "A pyramid approach to sub-pixel image fusion based on mutual information" Proceedings. International Conference on Image Processing (Cat. No. 96CH35919), Proceedings of 3rd IEEE International Conference on Image Proceeding, Lausanne, Switzerland, Sep. 16-19, 1996, pp. 265-268 vol. 1, XP010202198 1996, New York, NY, USA, IEEE , USA ISBN: 0-7803-3259-8.

Thevenaz P et al: "Spline pyramid for inter-modal image registration using mutual information" Wavelet Applications in Signal and Image Processing V, San Diego, CA, USA, Jul. 30-Aug. 1, 1997, vol. 3169, pp. 236-247, XP008021107 Proceedings of the SPIE—The International Society for Optical Engineering, 1997, SPIE-Int. Soc. Opt. Eng, USA ISSN: 0277-786X abstract.

Maintz, J.B.A. and Viergever, M.A. *A survey of medical image registration*. Medical Image Analysis, vol. 2, No. 1 (1998), pp. 1-36.

Tai, Y-C., Lin, K.P., Hoh, C.K., Henry Huant, S.C. and Hoffman, E.J. *Utilization of 3-D Elastic Transformation in the Registration of chest X-ray CT and Whole Body PET.* IEEE Transactions on Nuclear Science, vol. 44, No. 4 (Aug. 1997), pp. 1606-1612.

Sato, M., Hassanien, A-E., and Nakajima, M. *Non-linear registration of medical images using Cauchy-Navier splines transformation.* SPIE Conference on Image Processing, vol. 3361, (Feb. 1999), pp. 774-781.

Mattes, D. *Automatic Multimodality Image Registration with Deformations.* Thesis for the degree of master of Science in Electrical Engineering, Department of Electrical Engineering, University of Washington Medical Center, 2000, Seattle, Washington.

Viola, Paul A. *Alignment of Maximization of Mutual Information.* Thesis for the degree of Doctor of Philosophy, Artificial Intelligence Laboratory, Massachusetts Institute of Technology, 1995, Cambridge, Massachusetts.

Collignon, A., Maes, F., Delaere, D., Vandermeulen, D., Suetens, P. and Marchal, G. "Automated Multi-Modality Image Registration Based on Information Theory." in: Bizais, Y. et al. *Information Processing in Medical Imaging*, (Netherlands, Kluwer Academic Publishers, 1996) pp. 263-274.

Studeholme, C., Hill, D.L.G., and Hawkes, D.J. *An overlap invariant entropy measure of 3D medical image alignment. Pattern Recognition* vol. 32 (1999), pp. 71-86.

Rueckert, D., Sonoda, L.I., Hayes, C., Hill, D.L.G., Leach, M.O. and Hawkes, D.J. *Nonrigid Registration Using Free-Form Deformations: Applications to Breast MR Images.* IEEE Transactions on Medical Imaging, vol. 18, No. 8 (Aug. 1999), pp. 712-721.

Pluim, J.P.W., Maintz, J.B.A., and Viergever, M.A. *Image Registration by Maximization of Combined Mutual Information and Gradient Information.* IEEE Transactions on Medical Imaging, vol. 19, No. 8 (Aug. 2000), pp. 809-814.

Hellier, P. *Recalge non rigide en imagerie cerebrale: methodes et validation .* Thesis for the degree of Doctor of Philosophy, Universite de Rennes I, 2000, Rennes, France.

Masutani, Y. and Kimura, F. "Modally Controlled Free Form Deformation for Non-Rigid Registration in Image-Guided Liver Surgery." in: *Medical Imaging Computing and Computer-Assisted Interventions.* (2001), pp. 1275-1278.

Masutani, Y. and Kimura, F. *A new modal representation of liver deformation for non-rigid registration in image-guided surgery. International Congress Series*, vol. 1230, (2001), pp. 20-26.

Geraud, T. *Segmentation des structures internes du cerveau en imagerie par resonance magnetique.* Thesis for the degree of Doctor of Philosophy, Ecole nationale superieure des elecommunications, (1998) Paris, France.

Maes, F., Collingnon, A., Vandermeulen, D., Marchal, G., and Seutens, P. *Multimodality Image Registration by Maximization of Mutual Information.* IEEE Transactions on Medical Imaging, vol. 16, No. 2 (Apr. 1997), pp. 187-198.

Segars, W.P., Lalush, D.S., and Tsui, B.M.W. *Modeling Respiratory Mechanics in the MCAT and Spline-Based MCAT Phantoms.* IEEE Transactions on Nuclear Science, vol. 48, No. 1 (Feb. 20010, pp. 89-97.

Black, M.J., and Rangarajan, A. *On the Unification of Line Processes, Outlier Rejection, and robust Statistics with Applications in Early Vision. International Journal of Computer Vision*, vol. 19, No. 1 (1996), pp. 57-91.

Camara, O., Delso, G., Bloch, I. *Elvaluation of a thoracic elastic registration method using anatomical constraints in oncology. P.:roceedings 2Joint Conference of the IEEE Engineering in Medicine and Biology Society and the Biomedical Engineering Society*, EMBS-BMES, Houston, Oct. 2002.

\* cited by examiner

REGISTRATION OF THORACIC AND ABDOMINAL IMAGING MODALITIES

CROSS-REFERENCE TO RELATED APPLICATIONS

This application claims priority from U.S. provisional patent application Ser. No. 60/369,681 filed Apr. 3, 2002.

STATEMENT REGARDING FEDERALLY SPONSORED RESEARCH OR DEVELOPMENT.

Not Applicable.

Reference to a "Microfiche Appendix."

Not Applicable.

BACKGROUND OF THE INVENTION

1. Field of the Invention

This invention relates to methods for correlating clinical thoracic and abdominal images obtained by positron emission tomography (PET) and computer tomography (CT).

2. Description of Related Art Including Information Disclosed Under 37 CFR 1.97 and 37 CFR 1.98

Computer tomography CT, which uses X-ray images, and magnetic resonance imaging (MRI), which generates images based on the chemical composition of anatomic structures, both generate a familiar image of anatomy, with bones sharply outlined, and organs with greater or lesser sharp outlines. Positron emission tomography (PET), on the other hand, provides images based on the metabolic uptake of a radioactively-labeled metabolic compound previously injected intravenously into a patient, for example, the uptake of fluorine-18 fluorodeoxyglucose (18-FDG). This compound, an analogue of glucose, has been shown to be preferentially located in cancerous lesions, both primary and metastatic. It is important clinically that CT and PET images be correlated or registered so that the clinician can determine where in the patient's anatomy the 18-FDG has become located in order to determine treatment and prognosis of the patient.

The fact that 18-FDG is a small molecule which is injected intravenously suggests the expectation that its location by PET would not be sharply delineated, as compared to the images derived from CT. In addition, the processes of obtaining the images also introduce difficulties in registration. In most cases the CT and PET images are derived by separate instruments and from a patient at different times. The CT image is derived in a few seconds from a patient typically with his or her arms above his or her head and while the patient is holding his or her breath. In contrast, the PET image is derived over a considerable longer period, about 30 minutes, from a patient typically with arms at his or her sides for greater comfort and, necessarily, undertaking normal respiration. This causes the internal organs to move considerably in the PET determination. In fact, the PET image is an image of moving organs integrated over time.

The problem of registering CT and PET images is particularly severe when thoracic and abdominal images are involved, as respiration, cardiac motion, and abdominal organ motion are all involved and act to confound the registration.

This patent application discloses an improved method for registering CT and PET images of the lungs, liver and kidneys.

A review of registration methods is found in Maitz et al. Maintz, J. B. A. and Viergever, M. A. *A survey of medical image registration. Medical Image Analysis,* Vol. 2, no. 1 (1998), pp. 1-36.

Tai et al. have developed and evaluated a non-rigid CT and whole body PET technique. One inherent problem of this method is that it does not take account of patient movement between CT and emission PET image acquisition. Tai, Y-C., Lin, K. P., Hoh, C. K., Henry Huant, S. C. and Hoffman, E. J. *Utilization of 3-D Elastic Transformation in the Registration of chest X-ray CT and Whole Body PET. IEEE Transactions on Nuclear Science,* Vol. 44, no. 4 (August 1997), pp. 1606-1612.

A point-to-point based matching methodology that uses the Cauchy-Navier spline transformation to model the deformable anatomical behavior associated with non-rigid thorax medical image registration applies a transformation to landmarks extracted from the two different modality images. Sato, M., Hassanien, A-E., and Nakajima, M. *Non-linear registration of medical images using Cauchy-Navier splines transformation. SPIE Conference on Image Processing,* Vol. 3361, (February 1999), pp. 774-781.

Mattes has proposed one solution to multimodality chest image registration involving model deformations with cubic B-Splines defined by placing a regular grid of control points over the volume and then modified by moving the control points. Mattes, D. *Automatic Multimodality Image Registration with Deformations.* Thesis for the degree of Master of Science in Electrical Engineering, Department of Electrical Engineering, University of Washington Medical Center, 2000, Seattle, Wash.

The measurement of image similarity has been used by Viola and Collignon to compute an estimation of mutual information using a Parzen window histogram. Viola, Paul A *Alignment by Maximization of Mutual Information.* Thesis for the degree of Doctor of Philosophy, Artificial Intelligence Laboratory, Massachusetts Institute of Technology, 1995, Cambridge, Mass. Collignon, A., Maes, F., Delaere, D., Vandermeulen, D., Suetens, P. and Marchal, G. "Automated Multi-Modality Image Registration Based on Information Theory." in: Bizais, Y. et al. *Information Processing in Medical Imaging,* (Netherlands, Kluwer Academic Publishers, 1996) pp. 263-274.

Mutual Information is an information theoretic measure that expresses how much information from one image is contained in another image. Normalized Mutual Information (NMI) was introduced by Studeholme et al. in order to prevent the actual amount of image overlap from affecting the measure of Mutual Information. Studeholme, C., Hill, D. L. G., and Hawkes, D. J. *An overlap invariant entropy measure of 3D medical image alignment.* Pattern Recognition Vol. 32 (1999), pp. 71-86.

NMI has been used by Rueckert et al. for the non-rigid registration of contrast-enhanced breast magnet resonance images (MRI). Registration is achieved by minimizing a cost function which represents a combination of the cost associated with the smoothness of the transformation and the cost associated with the image similarity. This registration algorithm is much better able to recover the motion and deformation of the breast than rigid or affine registration algorithms. Rueckert, D., Sonoda, L. I., Hayes, C., Hill, D. L. G., Leach, M. O. and Hawkes, D. J. *Nonrigid Registration Using Free-Form Deformations: Application to Breast MR Images. IEEE Transactions on Medical Imaging,* Vol. 18, no. 8 (August, 1999), pp. 712-721.

The idea of constraining transformations in voxel-based methods or mixing them with information provided by segmentation has previously been used in image processing. Pluim et al. proposed including spatial information by combining mutual information with a term based on the gradient of the images to be registered in a rigid or affine brain application. Pluim, J. P. W., Maintz, J. B. A., and Viergever, M. A. *Image Registration by Maximization of Combined Mutual Information and Gradient Information. IEEE Transactions on Medical Imaging*, Vol. 19, no. 8 (August 2000), pp. 809-814.

Hellier et al. introduced an anatomical segmentation of the cortex to limit the areas of interest, to accelerate the algorithm, and to refine the results in specified arenas, in a non-rigid brain image registration. Hellier, P. *Recalge non rigide en imagerie cerebrate: methodes et validation*. Thesis for the degree of Doctor of Philosophy, Universite de Rennes I, 2000, Rennes, France.

In two papers, Masutani et al. developed a method to better control the nodes of Free Form Deformations (FFD) for non-rigid registration application in image-guided liver surgery. They worked with a combination of modal representation and FFD, moving grid control points surrounding the liver shape mode in several modes (rotation, translation, bending and twisting) to provide volumetric deformation. Masutani, Y. and Kimura, F. "Modally Controlled Free Form Deformation for Non-Rigid Registration in Image-Guided Liver Surgery." in: *Medical Imaging Computing and Computer-Assisted Interventions*. (2001), pp. 1275-1278. Masutani, Y. and Kimura, F. *A new modal representation of liver deformation for non-rigid registration in image-guided surgery. International Congress Series*, Vol. 1230, (2001), pp. 20-26.

Geraud has developed the idea of progressive structure recognition in cerebral tissue classification applications. Geraud, T. *Segmentation des structures internes du cerveau en imagerie par resonance magnetique*. Thesis for the degree of Doctor of Philosophy, Ecole nationale superieure des elecommunications, (1998) Paris, France.

Maes et al. proposed the use of a trilinear partial volume distribution interpolation method which provided an analytic form of the mutual information gradient, allowing the possibility of using gradient-based techniques to optimize the cost function. Maes, F., Collingnon, A., Vandermeulen, D., Marchal, G., and Suetens, P. *Multimodality Image Registration by Maximization of Mutual Information. IEEE Transactions on Medical Imaging*, Vol. 16, no. 2 (April, 1997), pp. 187-198.

Segars et al. has used a spline-based Mathematical Cardiac Torso (MCAT) to model movements of thoracic structures due to the respiratory cycle, thereby adding a new constraint to the deformations. Segars, W. P., Lalush, D. S., and Tsui, B. M. W. *Modeling Respiratory Mechanics in the MCAT and Spline-Based MCAT Phantoms. IEEE Transactions on Nuclear Science*, Vol. 48, no. 1 (February, 2001), pp. 89-97.

Black et al. has introduced M-estimators in the cost function to take account of the percentage of points that do not follow a model, called outliers. Black, M. J., and Rangarajan, A. *On the Unification of Line Processes, Outlier Rejection, and robust Statistics with Applications in Early Vision. International Journal of Computer Vision*, Vol. 19, no. 1 (1996), pp. 57-91.

U.S. Pat. No. 5,299,253 discloses a process of registering abdominal CT and MR images with single photon emission computed tomography (SPECT). The torso is immobilized and external contrasting markers used for the registering.

U.S. Pat. No. 5,608,221 discloses a dual head nuclear camera with SPECT and positron emission tomography (PET) systems. The non-uniformity of the absorption in the body is corrected for by transmission computed tomography (TEM) which uses an external source to assess the variable absorption and correct the resulting SPECT image.

U.S. Pat. No. 5,750,991 discloses a system for moving an external radiation source in a helical path about the patient for the purpose of determining the attenuation correction to account for non-uniformity of absorption. A discrete spherical source is transported by fluid through a tube coiled about the patient.

U.S. Pat. No. 5,871,013 discloses apparatus which produces a single photon transmission computerized tomography (SPTCT) image and a SPECT image simultaneously termed simultaneously transmission and emission tomography (STET). The STET image is registered with other modality images, such as MRI, ultrasound, x-ray CT. The process of registering STET and CT images involves taking the SPTCT image and transforming it to register with the CT image and then using the same parameters to register the STET and CT images. Body structures (such as bones) appearing in both the CT and SPTCT form the basis for the transformation.

U.S. Pat. No. 5,974,165 discloses methods for aligning and correlating images from two different modalities. The apices of the lungs are used to register radionuclide and radiographic images. The images are scaled to provide equal effective pixel size in each image.

U.S. Pat. No. 6,040,580 expands on the disclosures of U.S. Pat. No. 5,750,991.

U.S. Pat. No. 6,173,201 discloses a rigidly secured frame placed on a patient. A number of markers located on the frame are used in registering CT or MRI images with SPEC or PET images.

U.S. Pat. No. 6,405,072 discloses a system with cameras which record markers or natural landmarks on a body in 3D space. It is used for x-ray, CT, MRI, or PET imaging. Provisions are made for patient movement in respiration. Segmentation also is used.

Published U.S. Pat. Application No. 2002/0068864 discloses a process for assessing cardiac condition by the speed of removal of an injected radioactive solution from the left ventricle. Ultrasound, MRI, x-ray, CT, PET or SPEC images are used to locate the left ventricle region.

BRIEF SUMMARY OF THE INVENTION

In general, the objective of image registration applications is to perform the mapping of the data contained in one image into the other, in the present case, functional information provided by PET into the anatomically accurate CT scan. This means finding the geometric transformation which best aligns homogenous voxels in both images. A registration process has been defined in a mathematically as follows:

$$\check{T} = \arg\max_{T} S(I, T(J))$$

Where I, J are the two images or volumes to register, and $\check{T}$ is the transformation which maximizes an appropriately chosen similarity measure between images to register in a defined transformation space, with S the similarity function that provides this measure.

Concerning the transformation, in many cases a satisfactory solution can be found by using rigid registration, i.e. one of the data volumes is only translated and rotated to align it with the other with six degrees of freedom, such as in some brain applications. Global differences between images also can be modeled by a 3D affine spatial transformation with up to 12 free parameters. Such applications are effective in brain imaging because of the relative immobility of the organ imaged. However, in thoracic and abdominal applications, due to local deformations, movement of the organs, and the high variability of acquisitions, a non-rigid approach with significantly more degrees of freedom is needed.

Regarding the similarity measure, two apparently opposed approaches are used: segmentation-based and intensity-based. Segmentation-based methods rely on a preprocessing step to locate the same anatomical structures on both images, so that they can be used as a reference to perform the registration. These methods are reasonably quick and robust, but their accuracy is limited due to possible segmentation errors. This drawback is especially aggravated in the case of multi-modal registration, where the anatomical equivalence of the segmented structures must be assured. On the other hand, intensity-based methods use a similarity measure that integrates the whole gray-level content of the images, thus significantly increasing the precision that can be achieved. Nevertheless, this increase in precision induces a higher complexity of the maximization process, which implies slower convergence times and the risk of getting trapped in local minima if a good initialization was not provided.

This patent application discloses a method that integrates both approaches within a nonlinear transformation framework, taking advantage of the speed and robustness of the segmentation-based method to compensate for the worse deformation, such as those due to respiratory artifacts, and then using the intensity-based method to do the fine tuning of the results. This process combines the advantages of both segmentation and intensity-based methods while effectively canceling each method's drawbacks.

To solve the difficulties of registering anatomical and functional images, some common characteristics of the images were exploited, such as the approximate gray-level homogeneity of each organ in each image, and the spatial relationships between the organs, which are less sensitive to the deformations than the characteristics of the organs themselves.

Combined PET-CT machines were introduced by scanner constructors to bypass some of the difficulties, allowing acquisition of anatomical and functional information in the same examination, furnishing a hardware, or mechanical, rigid registration. The only remaining potential registration errors in such systems are due to physiological motion, in the chest, predominantly caused by breathing, except in the vicinity of the heart, and due to insufficient patient cooperation.

In general, the choice of the similarity criterion has been dealt with from two apparently opposed viewpoints. Methods based on anatomical information rely on a detection or segmentation step to extract some anatomical references which allow establishment of a registration. These methods, while conceptually simple and robust, have the common drawback of propagating to their final result those errors introduced by the segmentation step, significant errors due to the noisy and imprecise nature of medical images. Other methods count on the minimization of certain criteria that take in account the whole of the information contained in the images to achieve a better precision of the final registration. These methods tend to become trapped in local minima of the chosen criterion if the methods are not initialized within a relatively narrow range near to the desired solution.

In the present invention, a segmentation method is used with a nonrigid deformation framework to coarsely deal with the largest displacements during the first steps of the registration process, and a whole information method is used to fine tuning the results by using the detailed gray level information. This combination usage of both methods uses the advantages of both while canceling the drawbacks of each.

The process of registering an anatomical image of the thorax and abdomen of a patient with a functional image of the thorax and abdomen of the patient comprised the following steps. An anatomical image of the thorax and abdomen of the patient was obtained. A functional image of the thorax and abdomen of the same patient also was obtained. The anatomical features of the images were segmented. The functional image is in fact a combination of two images which includes the functional image as described above and a tissue density image derived by transmission of irradiation through the entire thickness of the patient's body. The tissue density image is used to correct the functional image for absorption by the patient's body. In addition, the tissue density image contains anatomical information which are used in the segmentation of the anatomical and functional images. A coarse registration of the anatomical and functional images was obtained by a process comprising the following steps. The scans were transformed using nonrigid B-Spline free form deformations using the anatomical features extracted from the anatomical and functional images. The root mean square difference of corresponding pixel gray levels of the transformed scans and the segmented anatomical features were minimized. The gradient descent of the positions of all the control points was minimized. The anatomical and functional images were put into fine registration in a process comprising the following steps. The results of the coarse registering and the functional scan were transformed using nonrigid B-Spline free form deformations. The information from one image contained in the other image was maximized using normalized mutual information and the results of the coarse registering and the anatomical scan. The gradient descent of the position of all the control points was minimized, and finally, the registered anatomical and functional images were displayed.

The objective of this invention is to provide a method for accurate registering of anatomical and functional images of the thorax and abdomen.

Another objective of this invention is to provide a method for accurate registering of anatomical and functional images of the thorax and abdomen which involves a minimum of computation.

Another objective of this invention is to provide a method for accurate registering of anatomical and functional images of the thorax and abdomen which accommodates the movement of organs depicted in the images.

Another objective of this invention is to provide a nonrigid method for accurate registering of anatomical and functional images of the thorax and abdomen.

Another objective of this invention is to provide a method for accurate registering of anatomical and functional images which exploit the spatial relations between organs.

Another objective of this invention is to provide a method for accurate registering of anatomical and functional images which uses nonrigid registration combining segmentation-based and intensity-based methods.

A final objective of this invention is to provide a method for accurate registering of anatomical and functional images which is rapid, requires minimal computational facilities, and is inexpensive to operate.

DETAILED DESCRIPTION OF THE INVENTION

Figure 1:
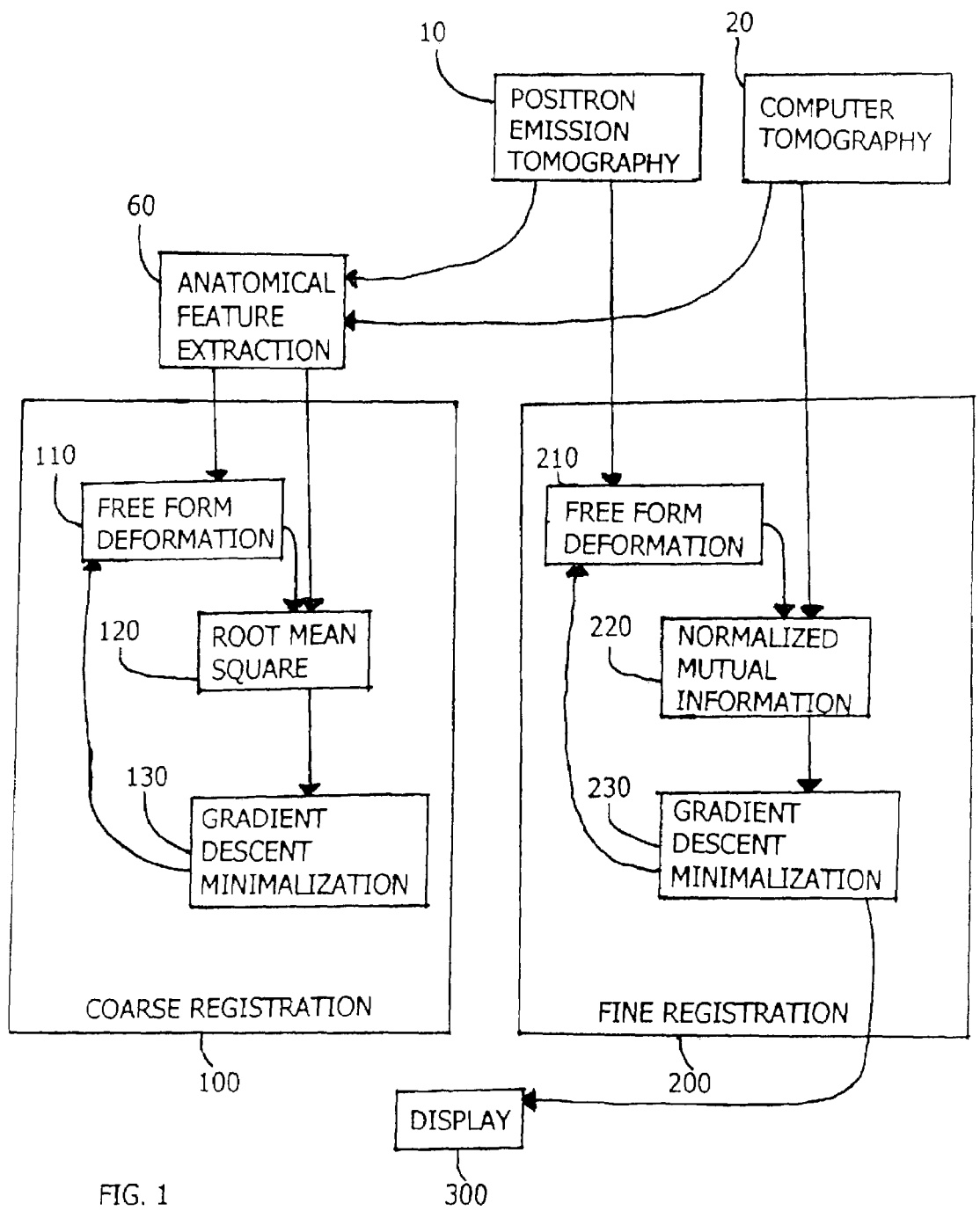
FIG. 1 is a schematic of the steps for the nonrigid registration of CT and PET scans.

In this patent application, the term "anatomical image" refers to methods of obtaining medical images with highly resolved anatomic features, such as by X-ray, computer tomography (CT), magnetic resonance imaging (MRI) and ultrasound (US). The term "functional image" refers to methods of obtaining images by methods which depend on the behavior of injected chemicals in the body, such as positron emission tomography (PET) and single photon emission transmission computerized tomography (SPECT). In the Figures which are schematic diagrams of processes, rectangles represent processes or steps in a process, and arrows represent the flow of data or digital information.

The processes of this invention provide accurate registration of anatomical and functional images with a minimal of computation and time required for computation. These processes are especially useful in the diagnosis and treatment of cancer located in the thorax and abdomen and in the diagnosis and treatment of heart diseases.

Any suitable instruments for determining anatomical and functional images may be used with the processes of this invention. A preferred CT system, is the GE Imatron C300 EBT scanner, which may be obtained from General Electric Medical Systems, Waukesha Wis. A preferred PET system is the GE Advance Whole Body PET System, which may be obtained from General Electric Medical Systems, Waukesha Wis. A preferred combination PET-CT acquisition system, is the Discovery LS PET/CT System, obtained from General Electric Medical Systems, Waukesha Wis.

FIG. 1 is a schematic of the steps of the method for the nonrigid registration of CT and PET scans of the present invention. In general, the left part, termed coarse registration, initialization or stage one 100 corresponds to the steps involved in finding an initial coarse registration of the scans by optimizing a deformation between segmented structures in both scans or images. The right part, termed fine registration, optimization, or stage two 200, corresponds to the subsequent steps which performs a refined registration by optimizing deformation between the whole intensities images.

In operation, digital data were extracted from a PET scan 10 and a CT scan 20, both scans of the thoracic and abdominal region of the same patient. The functional image is in fact a combination of two images which includes the functional image as described above and a tissue density image derived by transmission of irradiation through the entire thickness of the patient's body. The tissue density image is used to correct the functional image for absorption by the patient's body. In addition, the tissue density image contains anatomical information which is used in the segmentation of the anatomical and functional images. These data then were processed by anatomical feature extraction 60. In this process the main anatomical features, skin, lungs, skeleton, kidney, and liver are identified, if possible. The data then were processed in stage one 100.

In stage one 100 the data undergo iterative free form deformation processes based on B-Splines (FFD) 110. In all deformation processes, the CT images are not deformed but the PET images are deformed. These processes involve k-means automatic shareholding steps which resulting in a first approximation to the registration. These processes include translation and rotation, independent scaling in three axes, and cropping out parts of the volumes without correspondence between the PET and CT images.

The data were further refined by tuning the control points to minimize the root mean square (RMS) 120 difference of corresponding pixel gray levels, summed across the whole volume.

The coarse registration data next were optimized by minimizing the gradient descent minimization (GDM) 130 by iteratively applying a gradient descent technique simultaneously to the positions of all the control points. Intersection of nodes was prevented by application of a local spring force regularization term.

After iteration between the FFD, RMS, and GDM processes resulted in optimum coarse registration data, the fine registration process was initiated. The transition betweeen the coarse registration and fine registration processes was initiated when the RMS difference of corresponding pixels gray levels reached a predetermined minimum.

The fine registration, optimization, or stage two 200 process involves further treatment by FFD deformation based on B-Splines 210 of the data from stage one 100 and the PET scan 10.

Data from the FFD 210 step and the CT data were refined using normalized mutual information (NMI) 220 as a similarity measure.

The data from the NMI 220 step were further optimized by minimizing gradient descent (GDM) 230.

After iteration between the FFD, NMI, and GDM processes resulted in optimum fine registration data, the registered images were displayed 300 as registered CT and PET scans. The display process was initiated when the NMI similarity measure reached a predetermined maximum.

In a second embodiment process, data from the FFD 210 step and the CT data were refined not by using NMI as a similarity measure, but instead using Parzen windows to obtain a more robust computation of probability densities, smoothing them in order to allow for an estimation of the criterion derivative. These data were further treated as in the first embodiment. The display process was initiated when the Parzen windows probability densities reached a predetermined maximum.

The steps of the fine registration process 200 were repeated until optimum registration was obtained. The results were displayed 300 as registered CT and PET scans.

A nonrigid transformation based on B-Spline Free Form Deformations (FFD) 110 was used to establish correspondence between the scans in the coarse registration; and the same process 210 was used to refine the coarse registration and establish correspondence between the scans in the form of whole intensities images.

This FFD method was selected over more constrained parametric models because of the great variability of the anatomical structures in the thoracic and abdominal. FFDs make no assumptions on the underlying anatomy. In practical applications of registration methods, the registration process cannot take longer than the data acquision process. The relatively short computational time requirements for FFD methods make these preferable to other more realistic and time consuming deformation frameworks, such as elastic or fluid models.

Deformations of the object volume are achieved by tuning an underlying mesh of control points. The control point displacements are then interpolated to obtain a smooth and continuous C2 transformation. A B-Spline based FFD is written as a 3D tensor product of one-dimensional cubic B-Splines. Let $\Phi$ denote a uniformly spaced grid of $n_x \times n_y \times n_z$ control points $\phi_{i,j,k}$ with a spacing of $\delta$, where $-1 \leq i < n_x-1$, $-1 \leq j < n_y-1$, $-1 \leq k < n_z-1$. Then, the elastic transformation for each image point x,y,z is computed:

$$T_{elast}(x, y, z) = \sum_{l=0}^{3}\sum_{m=0}^{3}\sum_{n=0}^{3} B_l(u)B_m(v)B_n(w)\varphi_{i+l,j+m,k+n}$$

Here i,j, and k denote the index of the control point cell containing (x,y,z) and u, v, and w are the relative positions of (x,y,z) in the three dimensions, $B_0$ through $B_3$ being ID cubic B-Splines.

The unidimensional cubic B-Spline is defined as $$B_0 = (1-U)^3/6$$

$$B_1 = (3u^3 - 6u^2 + 4)/6$$

$$B_2 = (-3u^3 + 3u^2 + 3u + 1)/6$$

$$B_3 = u^3/6$$

A very convenient property of B-Splines is that they have a limited support, thus allowing local control of the transformation, which significantly reduces the amount of computation needed during the optimization process. Since this compact support can be separated as a tensor product, the B-Spline can be precalculated and stored in an array to accelerate the calculation process.

Stage One. Coarse Registration.

The goal of the stage one 100 is to take as much advantage as possible of the anatomical information in the images to constrain the search for the global solution which will undergo the next stage two 200. Stage one can be seen as an anatomical multiresolution step, filtering out of the data all but the main anatomical structures. The results of the registration of stage one is sent to stage two where finer anatomical detail is considered.

The efficiency of stage one depended on the anatomical information that could be extracted from the data in the CT and PET scans. Unlike segmentation-driven registration methods, the errors introduced during the segmentation step were not propagated in the final resulting registration, as the fine registration of stage two corrected these errors. Therefore it was not necessary that the system fully automatically segment both CT and PET scans, but a reasonably good approximation of those anatomical structures visible in both scans or, as many references about these structures as could be detected, were required. The objective of stage one was speed and reliability rather than accuracy.

A hierarchical procedure consisting of several segmentation steps aimed at progressively classifying different anatomical structures, using information from the most distinct features to restrict the segmentation of subtler features, was developed as a compromise between speed and quality of segmentation. Anatomical features to be taken into consideration, in decreasing order of significance, are: skin, lungs, skeleton, kidney, and liver.

The segmentation of the above organs is achieved through a series of several k-means automatically thresholding steps followed by mathematical morphology steps to be described below. Each thresholding step is followed by a verification of the consistency of the results which check for certain parameters of the extracted organs, such as dimensions, volume, or density, to be sure they are in the expected range.

For example, once the skin, skeleton, and lungs have been detected the kidney was segmented as follows. Firstly, the region of the search was bounded in the axial plane using the chest dimensions from the segmentation of the skeleton. Upper and lower bounds in the z axis were roughly estimated from the diaphragm position and lung dimensions. The backbone axis could also be used, although seldom required. Within the defined regions, a first automatic thresholding step was performed, followed by a verification of the dimensions and volume of the biggest components detected. If necessary, this thresholding step was repeated until the dimensions and volume were within the acceptable range. The detected region was dilated and applied as a mask on the original image. A second thresholding step was then applied to this masked image in an attempt to further refine the segmentation.

Although this process is simple and straightforward, it requires further refinement to be most useful. One problem is that the desirable lack of a priori anatomical knowledge about the shape of an organ in the process does make it more difficult to define the boundaries of organs when insufficient image resolution or movement of patient made it impossible to determine the edges of the organs. Another deficiency is the lack of a regularization term that limits the amount of detail obtainable from the images. This has proven a problem in the case of subtle structures such as the bronchia, which could be detected in the CT iscan but not in the PET, thus introducing a difference that the registration process wrongly interpreted as a deformation and incorrectly tried to compensate.

A 3D parametric deformable model has been implemented to refine the results obtained by the automatic thresholding step. Deformable models are curves or surfaces defined within an image that evolve under external force, computed from the image data, but under certain constraints expressed as internal forces. A 3D active contour is a parameterized surface such as:

$$X(u,v) = [x(u,v), y(u,v), z(u,v)]^t \text{ where } u \in [0,1], v \in [0,1].$$

The energy associated to this surface is composed by an internal energy term related to the physical properties of the model, and an external energy term that drives the model toward the desired features in the image.

$$E(X) = E_{int}(X) + E_{ext}(X)$$

The internal energy of the model is written as follows:

$$E_{int}(X) = \int_0^1 \int_0^1 \sum_{1 \leq i+j \leq k} \frac{(i+j)!}{i!j!} w_{ij}(u,v) \left\| \frac{\delta^{i+j} X(u,v)}{\delta u^i dv^j} \right\|^2 du\,dv$$

where $w_{ij}$ tune the elasticity and stiffness of the model and k is usually taken k=2, thus giving a second order regularization term. Our choice of an external energy is a weighted sum of a precomputed Gradient Vector Flow (GVF) field and a balloon force. Using GVF grants a smoother evolution of the model and an accurate convergence towards the organ surface even in the presence of concavities. A GVF field v(x) is defined as the equilibrium solution of the following vector diffusion equation:

$$u_t = g(|\Delta f|)\Delta^2 u - h(|\Delta f|)(u - \Delta f)$$

$$u(x,0) = \Delta f(x)$$

The first term of the first above equation is called the smoothing term, and tends to uniformize the resulting vector field. The second term is the data term and drives the vector field u towards the $\Delta f$ computed from the data. g( ) and h( ) are weighting functions that apply respectively to the smoothing and data term. The following terms are used:

$$g(|\Delta f|) = e^{\frac{-(|\Delta f|)^2}{K}}$$

$$h(|\Delta f|) = 1 - g(|\Delta f|)$$

This formulation allows for the gradient vector diffusion only where there are no strong edges, thus preventing the smoothing effect from averaging close opposing gradients, which could lead to a gap in the contour through which our model could leak.

The advantage of combining this GVF with a less accurate and potentially unstable balloon force is to avoid the computational cost of getting the 3D diffusion solution to reach beyond a band around the image edges. As a first segmentation approximation already has been performed, initiation of the contour within either the target organ or the attraction field of the GVF was insured. This expansion force significantly speeds up the process of driving the model towards a neighborhood of the edges in those cases where the previous segmentation step could not provide a good enough approximation of the organ boundary. Once in a neighborhood of the contour, GVF progressively takes the lead and the expansion term is switched off to avoid distorting the results. The danger of leaking through gaps in the organ contour is avoided because the GVF seals most of these gaps. The main concern at this stage is robustness rather than accuracy and the internal energy of the model is strong enough to keep the model from leaking through any remaining gaps.

Once the organs are segmented, they are used to automatically make a first approximation to the registration. This includes rigid motion (translation and rotation), independent scaling in the three axes, and cropping out those parts of the volumes without a correspondence between the images or interest in the application.

The first approximation to the registration was done using the previously described FFD deformation. The control points of the grid were tuned to minimize a given similarity criterion, the Root Mean Square (RMS) difference of corresponding pixels gray levels, summed across the whole volume, was used to determine the optimal deformation parameters.

Optimization of the deformation was achieved by applying iteratively a gradient descent technique simultaneously to the positions of all the control points. A local spring force regularization term was added to keep the nodes from intersecting.

Stage 2. Fine Resolution.

The coarse transformation of the first stage was modeled by a FFD based on B-Splines using Normalized Mutual Information (NMI) as a similarity measure. Such a method would tend toward local minima of the similarity criterion except for the fact that the coarse registration of the first stage provided an initial transformation very close to the final solution, at least in the neighborhood of segmented structure. Since the coarse transformation was not necessarily valid for regions away from the segmented anatomical structures, the second stage or fine registration phase was required. Another objective of the second stage was the correction of those errors that may have been introduced by the structure segmentation procedure by taking advantage of the image gray level information.

In the second stage, the FFD algorithm used in the first stage is used, but since the second stage uses the whole image intensity levels, the similarity criterion which is maximized is changed from the Root Mean Square to a variation of Mutual Information (MI) termed Normalized Mutual Information (NMI).

MI expressed how much information from an image I is contained in another image J. The advantage of this information-theoretic measure is that it computes the statistical dependence between image intensities of corresponding voxels, but without making assumptions regarding the nature of this dependence. Therefore, MI will be maximal in the images are geometrically aligned.

NMI prevents the actual amount of image overlap from affecting the measure.

$$NMI(I, J) = \frac{H(I) + H(J)}{H(I, J)}$$

Where $$H(X) = -\sum_{x \in X} p_x \log p_x$$

$$H(I, J) = -\sum_{i \in I} \sum_{j \in J} p_{i,j} \log p_{i,j}$$

where H (I) and H (J) are the marginal entropies of images and H (I,J) is their joint entropy, which is calculated from the joint histogram of I and J The computation of NMI required an estimation of the marginal and joint probability distributions from both CT and PET images. A frequency approximation was used, $p_{ij}=n_{ij}/n$, where $p_{ij}$ is the estimated probability of having an intensity i and j in the other, being $n_{ij}$ the number of voxels with these intensities and n the total number of voxels. An alternative method is to use the Parzen windowing to obtain a more robust computation of probability densities, smoothing them in order to allow for an estimation of the criterion derivative.

The procedure of optimization was based on a gradient estimation computed by local differences over the control point grid. For every control point, a one step displacement was performed, and the difference in NMI was computed. Then in each stage an iterative gradient descent technique was used to optimize. The overall process of the second stage fine resolution was speeded by including the anatomical multi-resolution of the first stage, which allowed skipping some of the time consuming lower multiresolution steps of the second stage.

EXAMPLE 1

A first set of 11 CT, emission and transmission PET scans of the thoracic and abdominal regions were analyzed using the method of this patent application. This was a inhomogeneous data set because the data were derived a three different sites and varying machines and clinical protocols were used. A second set of 4 images were obtained using a combination PET-CT acquisition system, the Discovery LS PET/CT System, obtained from General Electric Medical Systems, Waukesha Wis. The process used for analysis has been designed to be independent of the scan parameters. In general, the CT images had a resolution of 512×512 pixels in the xy plane and between 46 and 103 slices, with voxel dimensions approximately $0.74 \times 0.74 \times 7.5$ mm$^3$. PET images had a resolution of 128×128 pixels in the xy plane with 163 to 205 slices, with voxel dimensions around $4.297 \times 4.297 \times 4.297$ mm$^2$. In the PET-CT combined machine data set, the CT images had a resolution of 512×512 and the PET images 128×128 pixels in the xy plane, both having 205 slices. Voxel dimensions are $0.977 \times 0.977 \times 4.25$ mm$^3$ in CT and $3.906 \times 3.906 \times 4.25$ mm$^3$ in PET images.

A nonlinear registration evaluation protocol was devised to allow physicians to generate a semiquantitative measure3 of the registration accuracy. Several anatomically significant slices of both the original CT and registered PET volumes were presented to the evaluators. Each pair of images was marked with a ruler that defined some reference points as it crossed significant anatomical structures, such as the chest wall (ribcage), the mediastinal wall (heart), liver, stomach, and kidneys. These references allowed the clinician to estimate the difference in the position of the mentioned structures in both images. The registration was ranked in a scale going from 0 (good registration, error less than 0.5 cm) to 2 (unacceptable registration, error over 1.5 cm). The results for the first data set of 11 pairs are shown in Table 1.

TABLE 1

| Region | Mean | Variance (inter-patient) | Maximum | Minimum | Variance (inter-clinician) |
| --- | --- | --- | --- | --- | --- |
| Lungs | 0.522 | 0.02 | 0.64 | 0.30 | 0.001 |
| Heart | 0.597 | 0.11 | 1.44 | 0.30 | 0.005 |
| Liver | 0.467 | 0.15 | 0.87 | 0.16 | 0.006 |
| Stomach | 1.833 | 0.11 | 2 | 1.33 | 0.08 |
| Kidneys | 0.120 | 0.006 | 0.21 | 0.05 | 0.001 |

Table 1 shows performance of the method for the different anatomical regions. The low inter-clinician variance indicated that the evaluation method provides valid results. Table 1 shows excellent registration for lungs, heart, liver, and kidneys. Relatively poor registration was obtained for the stomach, probable because of the mobility of this organ.

The second set of images obtained using the combined CT-PET machine also were evaluated. Hardware registration achieved by these machines already was of high quality for two patients. For the other two patients, registration errors were found mainly over the cardiac region, which were partially corrected by the method of this invention application.

EXAMPLE 2

A third set of 18 CT, emission and transmission PET scans of the thoracic region were analyzed using the method of this patent application. This was a inhomogeneous data set because the data were derived a three different sites and varying machines and clinical protocols were used. The process used for analysis has been designed to be independent of the scan parameters. In general, the CT images had a resolution of 256×256 pixels in the xy plane and between 60 and 125 slices, with voxel dimensions approximately 1.0×1.0×5.0 mm$^2$. PET images had a resolution of 144×144 pixels in the xy plane with 160 to 230 slices, with voxel dimensions around 4.0×4.0×4.0 mm$^3$.

The evaluation method of Example 1 was used with Example 2. Table 2 shows the performance of this evaluation method for the different anatomical regions.

TABLE 2

| Region | Mean | Variance |
| --- | --- | --- |
| Chest Wall | 0.670 | 0.02 |
| Mediastinal Wall (heart) | 0.935 | 0.09 |
| Diaphragmatic Wall (liver) | 0.720 | 0.11 |

Table 2 shows that the evaluation method is repetitive enough to be used to validate the registration method of this patent application.

Table 3 shows the results of the evaluation of the registration of the third set of 18 CT and PET scans.

TABLE 3

| Region | Mean | Variance | Maximum | Minimum |
| --- | --- | --- | --- | --- |
| Chest Wall | 0.615 | 0.01 | 0.63 | 0.60 |
| Mediastinal Wall (heart) | 0.758 | 0.15 | 1.44 | 0.54 |
| Diaphragmatic Wall (liver) | 0.467 | 0.15 | 0.87 | 0.16 |

Table 3 shows excellent registration for chest wall, mediastinal wall (heart) and diaphragmatic wall (liver).

It will be apparent to those skilled in the art that the examples and embodiments described herein are by way of illustration and not of limitation, and that other examples may be used without departing from the spirit and scope of the present invention, as set forth in the appended claims.

We claim:

1. A process for registering an anatomical image of the thorax and abdomen of a patient with a functional image of the thorax and abdomen of the patient comprising the steps:
    a. obtaining an anatomical image of the thorax and abdomen of the patient using an X-ray, computer tomography, magnetic resonance imaging, or ultrasound scan,
    b. obtaining a functional image of the thorax and abdomen of the patient using a positron emission tomography or single photon emission transmission computerized tomography scan, the functional image containing functional and anatomical features,
    c. extracting the anatomical features of the anatomical and functional images,
    d. registering the anatomical and functional images by a process comprising the step:
        1. transforming the anatomical and functional images using nonrigid B-Spline free form deformations using the anatomical features extracted from the anatomical and functional images to compensate for largest deformations, and
        2. maximizing information from either the anatomical or functional image contained in either the anatomical or functional image using normalized mutual information.

2. A process for registering an anatomical image of the thorax and abdomen of a patient with a functional image of the thorax and abdomen of the patient comprising the steps:
    a. obtaining an anatomical image of the thorax and abdomen of the patient,
    b. obtaining a functional image of the thorax and abdomen of the patient, the functional image containing functional and anatomical features,
    c. extracting the anatomical features of the anatomical and functional images,
    d. coarse registering the anatomical and functional images by a process comprising the steps:
        1. transforming the seans anatomical and functional images using nonrigid B-Spline free form deformations using the anatomical features extracted from the anatomical and functional images,
        2. minimizing the root mean square difference of corresponding pixel gray levels of the transformed images and the segmented anatomical features, and
    e. fine registering the anatomical and functional images comprising the steps:
        1. transforming the results of step d. and the functional scan using nonrigid B-Spline free form deformations,
        2. maximizing the information from either the anatomical or functional image contained in either the anatomical or functional image using normalized mutual information and the results of step e. 1. and the anatomical scan, and f. displaying the registered anatomical and functional images.

3. The process of claim 2 wherein the anatomical image is a computer tomography scan.

4. The process of claim 2 wherein the functional image is a positron emission tomography scan.

5. The process of claim 2 wherein the anatomical image is a nuclear magnetic resonance scan.

6. The process of claim 2 wherein the anatomical image is an ultrasound scan.

7. The process of claim 2 wherein the anatomical features segmented are the skin, lungs, skeleton, kidney, or liver.

8. The process of claim 2 wherein the steps of step d. are repeated.

9. The process of claim 2 wherein the steps of step e. are repeated.

10. The process of claim 2 wherein step e. 2. is omitted and replaced by the following step:

e. 2A. maximizing the information from one image contained in the other image using Parzen windows and the results of step e. 1. and the anatomical image.

* * * * *